United States Patent [19]
Lover et al.

[11] 4,368,207
[45] Jan. 11, 1983

[54] HIGHER ALCOHOL TOXICANTS EFFECTIVE AGAINST INSECTS

[75] Inventors: Myron J. Lover, Mountainside; Arnold J. Singer, South Orange; Donald M. Lynch, Waldwick; William E. Rhodes, III, Cranford, all of N.J.

[73] Assignee: Block Drug Company Inc., Jersey City, N.J.

[21] Appl. No.: 955,707

[22] Filed: Oct. 30, 1978

Related U.S. Application Data

[63] Continuation of Ser. No. 802,014, May 31, 1977, abandoned.

[51] Int. Cl.³ ............................................ A01N 31/00
[52] U.S. Cl. ................................................... 424/343
[58] Field of Search ........................................ 424/343

[56] References Cited

U.S. PATENT DOCUMENTS 2,030,093  2/1936  Bousquet et al. .................. 424/343
3,226,295  12/1965  Goetz ................................ 424/343
3,943,234  3/1976  Roggenkamp ...................... 424/343

OTHER PUBLICATIONS

King; Chemicals Evaluated as Insecticides and Repellents at Orlando, Fla., May 1954, pp. 3-6,82,91,144,145,156,166,188,243 & 255.
King; Chemicals Evaluated as Insecticides and Repellents at Orlando, Fla., May 1954, pp. 136,186,190,202 & 241.

Primary Examiner—Allen J. Robinson
Attorney, Agent, or Firm—Ostrolenk, Faber, Gerb & Soffen

[57] ABSTRACT

Higher alcohols the logarithm of whose partition coefficient between n-octanol and water is at least 0.61 have been found to exhibit pediculicidal and/or ovicidal activity.

19 Claims, No Drawings

HIGHER ALCOHOL TOXICANTS EFFECTIVE AGAINST INSECTS

This is a continuation of application Ser. No. 802,014, filed May 31, 1977 now abandoned.

BACKGROUND OF THE INVENTION

There are only a relatively few pediculicides which are commercially available today. The most popular pediculicidal toxicants are Lindane (gamma benzene hexachloride), Malathion [(S-1,2-dicarbethoxyethyl)-0,0-dimethyl phosphorodithioate], synergized pyrethrins and Cuprex (a combination of tetrahydronapthalene, copper oleate and acetone, the acetone not asserted to be active). Because of increased concern about the overall safety of some of the known ectoparasitic toxicants, the search for new, safe and effective pediculicides has intensified recently.

In addition to killing insects, a good ectoparasiticide should also destroy ova to avoid a resurgence of the infestation. Surviving ova may hatch days or weeks after the initial treatment. Lacking ovicidal activity, a pediculicide safe to the host usually must be re-applied until control is achieved.

It has now been found that those higher alcohols which have a logarithm of their partition coefficient between n-octanol and water of at least 0.61 exhibit pediculicidal and/or ovicidal activity. These alcohols are known materials and have been incorporated into many pharmaceutical and costmetic preparations. For example, cetyl alcohol constitutes 15% of a published hair groom gel and 61% of a floating bath oil, and lauryl or isocetyl or dodecyl alcohol constitute about 30% of a mineral oil gel. Cetyl alcohol and lauryl alcohol are also listed under the United States Food & Drug Administration's approved Synthetic Flavor Substituents and Adjuvants list (Z1 CFR 1.1.1164). Cetyl alcohol has been used in compositions applied to the skin (U.S. Pat. Nos. 3,226,295 and 3,943,234) and lauryl alcohol derivatives have been used in parasiticides (U.S. Pat. No. 2,030,093).

It is the object of this invention to provide new, safe and effective toxicants for lice and their ova, and mites. This and other objects of the invention will become apparent to those skilled in the art from the following detailed description.

SUMMARY OF THE INVENTION

This invention relates to ectoparasiticidal toxicants and a method of controlling ectoparasites. More particularly, the invention relates to the use of certain higher alcohols as toxicants for lice and/or their ova and to toxicant compositions containing such higher alcohols.

DESCRIPTION OF THE PREFERRED EMBODIMENTS

The toxicants of the instant invention are monohydric alcohols, ROH, in which R is a substituted or unsubstituted alkyl group. The substituting moieties can be aryl, aryloxy halogen or the like. The R groups generally contain at least 4 carbon atoms and the maximum number of carbon atoms is not restricted but is generally 24 or less. It has been found that in order that the alcohols exhibit satisfactory pendiculicidal and/or ovicidal activity, the logarithm of the partition coefficient (hereinafter log P) for the compound between n-octanol and water must be at least 0.61. Log P values can be obtained by consulting Leo et al, *Chemical Review*, 71, 525 (1971) or calculated by the method therein described. When pediculicidal activity is desired, it is preferred that the alcohols be unsubstituted alkyl alcohols having log P values of 1.16–7.13. When ovicidal activity is desired, it is preferred that the alcohols have log P values of 1.1–7.13 and preferably are alkyl alcohols having log P values of 2.3–5.13. Accordingly, when both pediculicidal and ovicidal activity is desired, it is preferred to employ an unsubstituted alkyl alcohol having log P values of 2.13–5.1.

Typical of the monohydric alcohols which can be employed in this invention are n-butanol, sec-butanol, iso-butanol (but not tert-butanol), iso-pentanol, n-pentanol, n-hexanol, n-octanol, n-decanol, n-dodecanol, hexadecyl alcohol, oleyl alcohol, benzyl alcohol, 2-phenoxyethanol, cyclohexanol, 4-chlorobutanol, 2-phenylethanol, and the like.

One or more of the toxic alcohols of the present invention can be incorporated into an active toxicant composition which can be in the form of a liquid, powder, lotion, cream, gel, aerosol spray, or foam as the result of formulation with inert pharmaceutically acceptable carriers by procedures well known in the art. Any pharmaceutically acceptable carrier, whether aqueous or not aqueous, which is inert to the active ingredient can be employed. By inert is meant that the carrier does not have a substantial detrimental effect on the pediculicidal or ovicidal toxicant activity of the active ingredient.

The active alcohol is incorporated into the toxicant composition used to treat the substrate (human or animal) in need of such treatment, believed to be in need of such treatment, or desired to be prophylactically protected in an effective toxicant amount. By such amount is meant the amount which will cause at least 75% of the ectoparasites exposed in the two minute immersion tests described below to die within 24 hours in the case of lice and within 2 weeks in the case of the ova. The minimum concentration of alcohol in the composition required to provide an effective toxic amount varies considerably depending on the particular alcohol, the particular inert pharmaceutically acceptable carrier being employed and any other ingredients which are present. Thus, in one case a 10% concentration may suffice, while in other cases, concentrations as high as 30 to 40% may be required to obtain an effective toxic dose. The alcohols can also be employed as an adjuvant toxicant in a preparation which otherwise exhibits pediculicidal and/or ovicidal activity. In such preparations, the term "effective toxic dose" means that amount which will increase the mortality rate by about 20% in the standard immersion test.

The two minute immersion test referred to above is carried out as follows:

Pediculicidal activity: A 50 ml beaker is filled with tap water and allowed to come to room temperature (about 24° C.). Ten young adult male and ten young adult female lice (*Pediculus humanus corporis*) of the same age group and from the same stock colony are placed on a 2×2 cm coarse mesh patch. The sample to be tested, maintained at room temperature, is shaken until homogeneous and placed into a 50 ml beaker. The mesh patch is placed into the sample immediately after pouring, allowed to submerge, and after two minutes is removed and immediately plunged into the beaker containing the tap water. The patch is vigorously agitated every ten seconds and after one minute the patch is removed and placed on paper toweling. The lice are then transferred to a 4×4 cm black corduroy cloth patch and this point of time is considered zero hours. Thereafter, the corduroy patch is placed in a petri dish which is covered and stored in a 30° C. holding chamber.

Ovicidal activity: 15 adult, 5 to 10 day old, female lice (*Pediculus humanus corporis*) are placed on a 2×2 cm nylon mesh patch which is placed in a petri dish, covered and maintained in an incubator at 30° C. for 24 hours. The adult lice are then removed and the number of plump, viable eggs and shriveled, non-fertile eggs on the patch are recorded. The sample to be tested, maintained at room temperature, is shaken until homogeneous and poured into a 50 ml beaker. Immediately after the pouring, the mesh patch is placed into the beaker, allowed to submerge, and after two minutes is removed and immediately plunged into a 50 ml beaker containing tap water at room temperature (about 24° C.). The patch is vigorously agitated every ten seconds and after one minute, the patch is removed and placed on paper toweling for one minute. The patch is then placed in a petri dish which is covered and stored in the 30° C. incubator. Fourteen days following treatment, the number of hatched eggs and the number of shriveled or unhatched eggs is noted.

In both the pediculicidal and ovicidal two minute immersion tests, controls are run in identical manners to that described with room temperature (24° C.) tap water substituted for the sample to be tested. The results of the tests reported are net results.

In the following tables 1 and 2, the results of pediculicidal and ovicidal testing, respectively, for various alcohols of this invention and other alcohols are set forth. The alcohols were tested in undiluted form (100% alcohol), as a 25% solution in water, and in a solution containing 15% of the alcohol, 25% isopropanol and 60% aqueous ("15/25/60"). The results are set forth in terms of percent mortality.

TABLE 1

| Alcohol | Log P | Pediculicidal Rating 100% Alcohol | 25% Solution | 15/25/60 |
|---|---|---|---|---|
| Methanol | −0.66 | 0 | 0 | 0 |
| Ethanol | −0.32 | 45 | 0 | 0 |
| iso-Propanol | −0.12* | 65 | 0 | 0 |
| n-Propanol | 0.34 | 70 | 0 | 0 |
| tert-Butanol | 0.37 | 80 | 0 | 0 |
| sec-Butanol | 0.61 | 95 | 0 | 35 |
| iso-Butanol | 0.65 | 95 | 40 | 0 |
| n-Butanol | 0.88 | 100 | 20 | 0 |
| Benzyl Alcohol | 1.10 | 90 | 0 | 5 |
| iso-Pentanol | 1.16 | 100 | 55 | 80 |
| 2-Phenoxyethanol | 1.16 | 100 | 5 | 5 |
| Cyclohexanol | 1.23 | 100 | 0 | 20 |
| 4-Chlorobutanol | 1.27* | 100 | 0 | 20 |
| 2-Phenylethanol | 1.36 | 100 | 0 | 80 |
| n-Pentanol | 1.40 | 100 | 10 | 75 |
| n-Hexanol | 2.03 | 100 | 5 | 85 |
| n-Octanol | 3.15 | 100 | 10 | 85 |
| n-Decanol | 4.15* | 100 | 20 | 95 |
| n-Dodecanol | 5.13 | 100 | 10 | 100 |
| Hexadecyl Alcohol | ≦7.13* | 100 | 40 | 90 |
| Oleyl Alcohol | 7.47* | 100 | 0 | 40 |

TABLE II

| Alcohol | Log P | Ovicidal Rating 100% Alcohol | 25% Solution | 15/25/60 |
|---|---|---|---|---|
| Methanol | −0.66 | 4 | 27 | 0 |
| Ethanol | −0.32 | 4 | 7 | 13 |
| iso-Propanol | −0.12* | 1 | 0 | — |
| n-Propanol | 0.34 | 27 | 23 | — |
| tert-Butanol | 0.37 | 16 | 17 | 0 |
| sec-Butanol | 0.61 | 10 | 46 | 32 |
| iso-Butanol | 0.65 | 0 | 58 | 2 |
| N—Butanol | 0.88 | 48 | 17 | 2 |
| Benzyl Alcohol | 1.10 | 100 | 100 | 29 |
| iso-Pentanol | 1.16 | 100 | 52 | 0 |
| 2-Phenoxyethanol | 1.16 | 100 | 100 | 100 |
| Cyclohexanol | 1.23 | 100 | 0 | 57 |
| 4-Chlorobutanol | 1.27* | 100 | 100 | 100 |
| 2-Phenylethanol | 1.36 | 100 | 100 | 34 |
| n-Pentanol | 1.40 | 100 | 67 | 35 |
| n-Hexanol | 2.03 | 100 | 100 | 100 |
| n-Octanol | 3.15 | 100 | 100 | 100 |
| n-Decanol | 4.15* | 100 | 100 | 100 |
| n-Dodecanol | 5.13 | 100 | 100 | 100 |
| Hexadecyl Alcohol | ≦7.13* | 100 | 75 | 29 |
| Oleyl Alcohol | 7.47* | 84 | 0 | 20 |

The miticidal activity of the instant toxicants was determined as follows. Into a one cubic foot chamber, held at room temperature, is placed a covered microscope depression slide containing ten adult mixed sex mites, *Psoroptes equi* var. cuniculi. The slide is positioned at a distance of ten inches horizontally and four inches below the activator of a mechanical spray device and uncovered. The mechanical pump spray device delivers 50 micrograms of sample per depression of the activator. The sample to be tested, maintained at room temperature, is shaken until homogenous and placed in the mechanical pump spray device. The primed activator is depressed twice, releasing 100 micrograms of spray mist into the closed chamber. The mist is allowed to settle and the slide containing the mites is removed and covered. This point of time is considered zero hours. The covered slide is then held at room temperature for 24 hours. Microscopic observations are noted at 0, 1, 3, and 24 hours post treatment. Controls are run in an identical manner as that described using water or the diluting agent, and net mortality results are reported.

TABLE III

| Alcohol | log P | Miticidal Rating 100% Alcohol | 50% Solution in Isopropanol |
|---|---|---|---|
| iso-Propanol | −0.12* | 0 | — |
| sec-Butanol | 0.61 | 50 | — |
| n-Butanol | 0.88 | 100 | — |
| Benzyl Alcohol | 1.10 | 100 | — |
| Cyclohexanol | 1.23 | — | 100 |
| 2-Phenylethanol | 1.36 | 100 | — |
| n-Pentanol | 1.40 | 100 | — |
| n-Hexanol | 2.03 | 100 | — |
| Hexadecyl Alcohol | ≦7.13* | — | 100 |
| Oleyl Alcohol | 7.47* | 30 | — |

The log P values set forth in the foregoing tables I, II and III are those set forth in the aforementioned Leo et al article except for the values starred which were calculated using standard methods. The log P value for hexadecyl alcohol is a calculated value and the actual figure is dependent on the degree of branching of the alkyl moiety.

As noted above, various end use formulations can be prepared. Some typical formulations are set forth below and the amounts recited are percentages by weight:

| | |
|---|---|
| Clear colorless liquid suitable for mechanical spray application or inunction | |
| Isopropyl alcohol | 65 |
| Hexadecyl alcohol | 15 |
| Water | 20 |
| Clear shampoo | |
| Isopropyl alcohol | 25 |
| n-Dodecanol | 15 |
| Triethanolamine lauryl sulfate | 20 |
| Water | 40 |
| Lotion | |
| Isopropyl alcohol | 25 |
| Hexadecyl alcohol | 15 |
| Carboxypolymethylene | 0.1 |
| Triethanolamine | 0.1 |
| Water | 59.8 |
| Cream | |
| Isopropyl alcohol | 25.0 |
| Isopentanol | 15.0 |
| Glyceryl monostearat | 22.5 |
| Sorbitan monostearate | 1.5 |
| Polysorbate 60 | 3.5 |
| Xanthan gum | 0.2 |
| Water | 32.3 |
| Quick Breaking Aerosol Foam | |
| Mono and diglycerides from the glycerides of edible fats | 8 |
| n-Octanol | 15 |
| Isopropanol | 25 |
| Glycerine | 3 |
| Isobutane | 8 |
| Water | 41 |
| Powder | |
| 4-Chlorobutanol | 10 |
| Talc | 90 |
| Stick | |
| Sodium stearate | 8.0 |
| Sorbitol | 3.5 |
| Isopropanol | 25.0 |
| Ethanol | 39.0 |
| n-Decanol | 15.0 |
| Water | 9.5 |
| Gel | |
| Carboxypolymethylene | 1.5 |
| Isopropyl alcohol | 25.0 |
| 4-Chlorobutanol | 10.0 |
| Polysorbate 80 | 4.0 |
| Triethanolamine | 3.0 |
| Water | 56.5 |

Various changes and modifications can be made in the instant invention without departing from the spirit and scope thereof. The various embodiments set forth herein were for the purpose of further illustrating the invention and were not intended to limit it. Throughout this specification and claims, all parts and percentages have been by weight and all temperatures in degrees Centigrade unless otherwise indicated.

We claim:

1. A method of controlling mites which comprises applying to a human or animal host in need of such control, an effective toxic amount of at least one monohydric alcohol of 4–18 carbon atoms whose logarithm of the partition coefficient between n-octanol and water (log P) is at least 0.61.

2. The method of claim 1 wherein said alcohol has a log P of 1.1–7.13.

3. The method of claim 2 wherein said alcohol is an alkanol having a log P of 2.3–5.13.

4. The method of claim 3 wherein said alcohol is selected from the group consisting of octanol, decanol, dodecanol, and hexadecyl alcohol.

5. The method of claim 1 wherein said alcohol is employed in combination with an inert pharmaceutically acceptable carrier.

6. The method of claim 5 wherein said carrier is aqueous.

7. A method of controlling lice comprising applying to a human or animal host in need of such control, an effective toxic amount of a monohydric alcohol selected from the group consisting of iso-pentanol, 2-phenyl-ethanol, n-pentanol, n-hexanol, n-octanol and hexadecyl alcohol in an inert pharmaceutically acceptable carrier.

8. The method of claim 7 wherein said carrier is aqueous.

9. The method of claim 8 wherein said carrier contains isopropanol.

10. The method of claim 9 wherein said alcohol is iso-pentanol.

11. The method of claim 8 wherein said alcohol is 2-phenyl-ethanol.

12. The method of claim 9 wherein said alcohol is n-pentanol.

13. The method of claim 9 wherein said alcohol is n-octanol.

14. The method of claim 9 wherein said alcohol is hexadecyl alcohol.

15. A method of controlling Pediculus ova which comprises applying to a human or animal host in need of such control an effective toxic amount of a monohydric alcohol selected from the group consisting of n-hexanol, dodecanol, and hexadecyl alcohol in an inert pharmaceutically acceptable carrier.

16. The method of claim 15 wherein said carrier is aqueous.

17. The method of claim 15 wherein said alcohol is n-hexanol.

18. The method of claim 15 wherein said alcohol is dodecanol.

19. The method of claim 15 wherein said alcohol is hexadecyl alcohol.

* * * * *